(12) United States Patent
Winston et al.

(10) Patent No.: US 6,193,676 B1
(45) Date of Patent: Feb. 27, 2001

(54) GUIDE WIRE ASSEMBLY

(75) Inventors: Thomas R. Winston, Leawood; John M. Neet, Lawrence, both of KS (US)

(73) Assignee: IntraLuminal Therapeutics, Inc., Carlsbad, CA (US)

( * ) Notice: Subject to any disclaimer, the term of this patent is extended or adjusted under 35 U.S.C. 154(b) by 0 days.

(21) Appl. No.: 09/060,487

(22) Filed: Apr. 15, 1998

Related U.S. Application Data

(63) Continuation-in-part of application No. 08/943,386, filed on Oct. 3, 1997, now Pat. No. 5,951,482.

(51) Int. Cl.$^7$ .................................. A61B 5/00; G01B 9/02

(52) U.S. Cl. ........................... 600/585; 600/478; 356/345

(58) Field of Search ...................................... 600/585, 473, 600/476, 478, 505, 342; 606/3, 15; 356/345

(56) References Cited

U.S. PATENT DOCUMENTS 5,867,268 * 2/1999 Gelikonov et al. .................. 356/345

* cited by examiner

*Primary Examiner*—Marvin M. Lateef
*Assistant Examiner*—Shawna J Shaw
(74) *Attorney, Agent, or Firm*—Armstrong Teasdale LLP

(57) ABSTRACT

Systems and methods for guiding the advancement of a guide wire through body tissue are described. In one embodiment, the guide wire has a first end, a second end, or guide wire head, a bore extending between the first and second ends, and includes an interferometric guidance system. The interferometric guidance system includes a low coherent illumination source, an optical beam splitter, a first optic fiber, a second optic fiber, and a photodetector. Each optic fiber includes a first end and a second end, and is wrapped around a piezo electric transducer (PZT). The second optic fiber has a fixed reflector on the second end. The photodetector is configured to determine interference between a first reflected light beam propagating through the first optic fiber and a second reflected light beam propagating through the second optic fiber. In one embodiment, the guide wire second end is inserted into a blood vessel so that the first optic fiber second end is inserted in the vessel. The beam splitter splits a light beam from the illumination source into two beams which propagate separately along the first optic fiber and the second optic fiber. The beams are reflected from the optic fiber second ends, and are recombined at the beam splitter. Before advancing the guide wire further, sawtooth voltage signals are applied to the PZTs, causing the PZTs to alternately expand to contract and change the optical path length along the two optic fibers. The reflected light beams interfere constructively or destructively depending on their respective optical path lengths. By enabling the PZTs, various interferences are generated by changing the optical path lengths along the first and second optic fibers. The interference information is then processed to determine the safety of advancing the guide wire further into the blood vessel.

23 Claims, 1 Drawing Sheet

GUIDE WIRE ASSEMBLY

This is a continuation-in-part of prior application Ser. No. 08/943386, filed Oct. 3, 1997, now U.S. Pat. No. 5,951,482 issued Sep. 2, 1999, and incorporated herein by reference.

FIELD OF THE INVENTION

This invention relates generally to medical guide wires and catheters and more particularly, to guiding assemblies and guiding methods for guide wires.

BACKGROUND OF THE INVENTION

Disease processes, e.g., tumors, inflammation of lymph nodes, and plaque build-up in arteries, often afflict the human body. As one specific example, atherosclerotic plaque is known to build up in the walls of arteries in the human body. Such plaque build-up restricts circulation and often causes cardiovascular problems, especially when the build-up occur in coronary arteries.

To treat such disease, it often is necessary to guide a medical device to the diseased site, and then use the medical device to treat the diseased area. Often a guide wire is used to help guide other treatment devices. A guide wire typically is required to properly position a catheter in an artery. The guide wire is advanced and forms a path, through the artery and region of plaque build-up. The catheter or other device such as a balloon or rotational atherectomy device is then guided through the artery using the guide wire.

Known guide wires exist for the treatment of tissue. For example, known guide wires use laser energy to remove plaque build-up on artery walls as the guide wire is advanced One known catheter includes a laser source and a guide wire body. The guide wire body has a first end and a second end, or head, and several optic fibers extend between the first end and the second end. The laser source is coupled to each of the optic fibers adjacent the catheter body first end and is configured to transmit laser energy simultaneously through the optic fibers.

To remove arterial plaque, for example, the guide wire body is positioned in the artery so that the second end of the guide wire body is adjacent a region of plaque build-up. The laser source is then energized so that laser energy travels through each of the optic fibers and substantially photoablates the plaque adjacent the second end of the catheter body. The guide wire body is then advanced through the region to photoablate the plaque in the entire region.

However, it often is difficult to guide known guide wires through the body without risking damage. For example, known guide wires typically cannot be easily advanced through partially or totally occluded arteries without substantial risk of damaging or puncturing the artery wall. As the guide wire is advanced through the artery, it will encounter obstructions to advancement including plaque build-up or the artery wall itself. However, known guide wires typically do not distinguish between plaque build-up and the artery wall. An operator may therefore incorrectly identify an obstruction as plaque build-up and attempt to push the guide wire through the obstruction, resulting in injury or puncture of the artery wall.

Accordingly, it would be desirable to provide a guide wire including a guidance system to determine the safety of advancing the guide wire further into the vessel. In particular, it would also be desirable to provide such a guide wire with the capability of providing information to an operator to distinguish among the types of obstructions which might be hindering advancement of the guide wire.

SUMMARY OF THE INVENTION

These and other objects may be attained by a guide wire assembly which, in one embodiment, includes an interferometric guidance system. Particularly, the guide wire assembly includes a substantially cylindrical guide wire including a first end, a second end, or guide wire head, and a bore extending between the first and second ends. The interferometric guidance system is coupled to the guide wire and includes a low coherent illumination source, an optical beam splitter, a first optic fiber, a second optic fiber, a photodetector and a computer. The first optic fiber is wrapped around a first piezo electric transducer (PZT), and the second optic fiber is wrapped around a second PZT. The first PZT and second PZT are connected to the guidance system in reverse parallel configuration so that when a sawtooth voltage signal is applied, one expands while the other contracts. The first optic fiber includes a first end and a second end, and extends through the guide wire bore so that the second end is adjacent the guide wire second end. The second optic fiber of the guidance system similarly includes a first end and a second end, and a fixed reflector, such as a metal deposit reflector, on the second optic fiber second end.

The beam splitter includes an illumination source input, a first beam output, a second beam output, and a combined beam output. The illumination source is coupled to the illumination input of the beam splitter. The first end of the first optic fiber, and the first end of the second optic fiber are coupled to the beam splitter. Particularly, the first optic fiber first end is communicatively coupled to the first beam output of the beam splitter, and the second optic fiber first end is communicatively coupled to the second beam output of the beam splitter. The beam splitter combined beam output is coupled to the photodetector, which is communicatively coupled with the computer. The photodetector is configured to determine interference between substantially equal reflected light beams which are initially emitted from the same source and are later split to propagate separately through the first optic fiber and through the second optic fiber.

In operation, the guide wire head is inserted at least partially into, for example, a blood vessel so that the guide wire head and the first optic fiber second end of the guidance system is positioned outside the blood vessel. The beam splitter splits the illumination source light beam into two beams. The first beam is transmitted through the first optic fiber to the tissue located in front of the second end of the guide wire. The tissue, acting as a reflective surface, reflects at least a portion of the first light beam back into the first optic fiber and back to the beam splitter. The second light beam is transmitted through the second optic fiber to the fixed reflector which reflects the second light beam, and the reflected beam is returned to the beam splitter. The beam splitter combines the reflected first and second light beams, resulting in constructive or destructive interference of the two light beams, and creates a combined light beam output. The combined light beam output, including interference information, is coupled to the photodetector and the photodetector output is processed by the computer to determine the safety of advancing the guide wire second end, further into the vessel.

Prior to advancing the guide wire further into the vessel, out of phase frequency signals are applied to the PZTs, causing the PZTs to alternately expand and contract out of phase with one another. This action alternately stretches each optic fiber to extend its length. Specifically, alternating between extending the length of the first optic fiber and extending the length of the second optic fiber changes the length of the optical path for the first and second light beams. This shifts the interference point of the reflected first and second light beams, producing interference data which is processed to provide information regarding the tissue at known distances from the guide wire second end.

The above described guide wire assembly provides a guidance system to determine the safety of advancing a guide wire further into a vessel.

DETAILED DESCRIPTION

Figure 1:
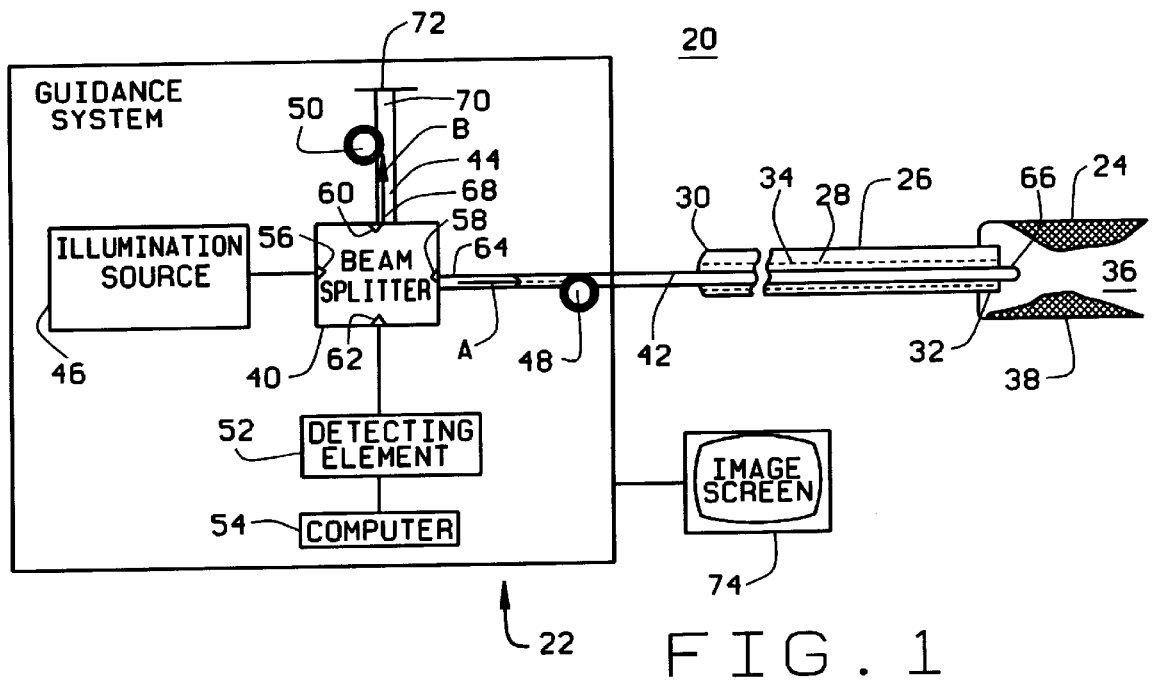
FIG. 1 is a pictorial illustration of a guide wire assembly in accordance with one embodiment of the present invention inserted into a blood vessel.

FIG. 1 is a pictorial illustration of a guide wire assembly 20 in accordance with one embodiment of the present invention. Guide wire assembly 20 includes an interferometric guidance system 22 and is configured to be inserted into a body passage 24 such as a blood vessel. Guide wire assembly 20 further includes a catheter 26 extending over a guide wire 28. Guide wire 28 has a first end 30 and a head 32, and includes a bore 34 extending between first end 30 and head 32. Guide wire second end 32 is positioned within an interior 36 of blood vessel 24 adjacent tissue through which guide wire 28 is to be advanced, e.g., plaque 38. Guide wire 28 may be formed, for example, with a coiled wire, as known in the art.

Guidance system 22 includes a beam splitter 40, a first, or measuring, optic fiber 42, and a second, or reference, optic fiber 44, an illumination source 46, two piezo electric transducers (PZTs) 48 and 50, a detecting element 52, and a computer 54. Beam splitter 40 includes an illumination source input 56, a first beam output 58, a second beam output 60, and a combined beam output 62. First optic fiber 42 includes a first end 64 and a second end 66, and is coupled to guide wire 28 so that second end 66 is adjacent guide wire head 32 and is positioned in blood vessel interior 36. First optic fiber second end 66 is glued to guide wire head 32, for example with epoxy. Second optic fiber 44 also includes a first end 68 and a second end 70. Second optic fiber second end 70 includes a fixed reflector 72. First optic fiber first end 64 is coupled to first beam output 58, and second optic fiber first end 68 is coupled to second beam output 60. First optic fiber 42 is configured to emit energy waves substantially coaxially with respect to guide wire head 32. In one embodiment, illumination source 46 is a low coherent illumination source, for example, a laser as known in the art.

Optic fibers 42 and 44 are fabricated from drawn or extruded glass or plastic having a central core and a cladding of a lower refractive index material to promote internal reflection. In one embodiment, optic fibers 42 and 44 are polarization-preserving optic fibers which preserve the plane of polarization of a light beam as it propagates along the length of a fiber. Polarization-preserving optic fibers maintain the polarization of the light beam by having asymmetry in the fiber structure, either in the overall shape of the fiber, or in the configuration of the cladding with respect to the central core. In one embodiment, the diameter of each fiber is about 80 microns, but the diameter may vary.

PZTs 48 and 50 are fabricated from piezoelectric material wrapped around a cylinder as known in the art, and are connected in guidance system 22 in reverse parallel configuration so that one PZT expands while the other contracts. PZT's 48 and 50 are configured so that expansion and contraction of the piezoelectric material changes the diameter of the PZT's. First optic fiber 42 and second optic fiber 44 are wrapped uniformly in layers around PZTs 48 and 50. In one embodiment, first optic fiber 42 is wrapped approximately 1000 times around PZT 48, and second optic fiber 44 is wrapped approximately 1000 times around PZT 50. The length of each optic fiber does not exceed about 110 meters. PZTs 48 and 50 are each configured to expand and contract, thereby changing in diameter, upon application of a voltage signal, for example, a sawtooth wave. In one embodiment, the voltage signal has a voltage of about 1 kV or below, and a frequency of about 10 hertz to about 30 hertz, with a current of less than 100 milliamps, although other voltage signal values may be used. In alternate embodiments, PZTs 48 and 50 may instead be other lengthening means for altering the length of first optic fiber 42 and second optic fiber 44.

In one embodiment, detecting element 52 is a photodetector coupled to an image screen 74 and configured to transmit data to image screen 74. Particularly, detecting element 52 is configured to determine interference between a light beam propagating through first optic fiber 42 and a light beam propagating through second optic fiber 44, and to generate interference data representative of such interference. For example, detecting element 52 may include a detector, a demodulator and an analog digitizer which cooperate in a known manner to generate such interference data. Such interference data is transmitted to computer 54 which generates image data for display on image screen 74 or to notify an operator operating by hand of an adverse situation and to discontinue pursuing the current path.

Figure 2:
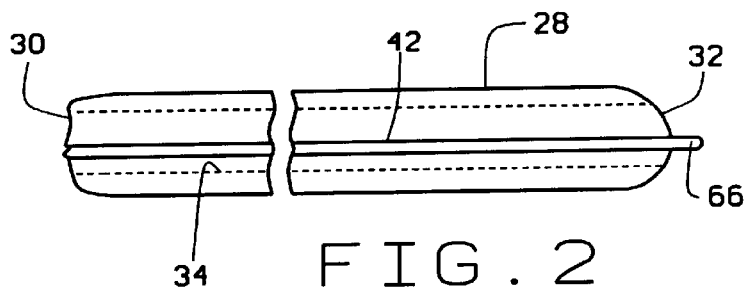
FIG. 2 is a sectional view of the guide wire shown in FIG. 1.

As shown more clearly in FIG. 2, guide wire 28 includes guide wire bore 34 extending between guide wire first and second ends 30 and 32, respectively. First optic fiber 42 extends through guide wire bore 34 so that second end 66 of first optic fiber 42 is adjacent guide wire second end 32. In one embodiment, second end 66 is flat polished.

Figure 3:
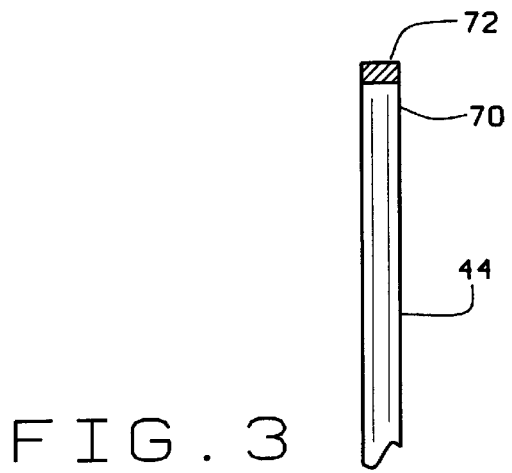
FIG. 3 is a schematic illustration of a fixed reflector on the second optic fiber.

Referring now to FIG. 3, second optic fiber second end 70 includes fixed reflector 72. In one embodiment, second optic fiber second end 70 is polished flat and fixed reflector 72 is fabricated by depositing gold onto second optic fiber end 70 using depositing methods known to those skilled in the art. In alternate embodiments, fixed reflector 72 may be fabricated from any material having a different refractive index than second optic fiber 44, or may be another type of mirror known in the art. Noble metals such as gold, platinum and silver are inert, yield good reflections and are therefore especially suitable for reflector 72, but other suitable materials may be used.

In use and referring again to FIG. 1, guide wire assembly 20 is inserted into blood vessel 24, using catheter 26, so that guide wire second end 32 and first optic fiber second end 66 are positioned within blood vessel 24, and second optic fiber second end 70 is positioned outside blood vessel 24, and outside the body.

Light beam source 46 transmits a light beam to beam splitter 40, which splits the light beam into first and second substantially equal light beams A and B, respectively. First light beam A is then transmitted through first optic fiber 42 and second light beam B is transmitted through second optic fiber 44. First light beam A exits from first optic fiber second end 66 substantially coaxially with respect to guide wire head 32, is at least partially reflected by the tissue, re-enters first optic fiber second end 66 and propagates toward first optic fiber first end 64. Similarly, second light beam B transmitted through second optic fiber 44 is at least partially reflected by reflector 72, re-enters second optic fiber second end 70 and propagates toward second optic fiber first end 68. Light beams A and B are recombined at beam splitter 40 and directed to photodetector 52.

Upon recombining at beam splitter 40, light beams A and B interfere constructively or destructively with each other depending on the relative lengths of their optical paths and the coherence function of source 46. The optical path length of light beam A depends on the length of first optic fiber 42 and the distance of the reflecting tissue within the blood vessel from first optic fiber first end 66. The optical path length of light beam B depends on the length of second optic fiber 44. For example, when light beam A travels an optical path equivalent in length to the optical path length travelled by light beam B, the two light beams exhibit maximum constructive interference when recombined at beam splitter 40. Similarly, constructive interference can be eliminated by changing the relative optical path lengths of light beams A and B, by enabling PZTs 48 and 50 and stretching the optic fibers. Specifically, out-of-phase voltage signals are applied to PZTs 48 and 50, causing PZTs 48 and 50 to alternately expand and contract and thereby increase and decrease the optical distances along the optic fibers. In particular, alternating between increasing the optical distance along first optic fiber 42, and increasing the optical distance along second optic fiber 44, shifts the interference point of the reflected light beams A and B.

The pattern of interference as the voltage signal is applied to the PZTs 48 and 50 is processed to provide interference points to provide the operator with information to determine if guide wire 28 can be safely advanced.

In one embodiment, the PZT has a diameter of one inch, and each wrap of an optic fiber around a PZT stretches the optic fiber approximately 10 microns. When the PZT is expanded in response to an applied voltage signal of about 1 kV or below, 300 wraps of the optic fiber around the PZT provide a working viewing range of approximately 1 millimeter The combined working viewing range of PZTs 48 and 50 connected in reverse parallel configuration provide a working viewing range of about 2 mm. In another embodiment, each optic fiber is wrapped around a PZT 1000 times, thereby providing a range of approximately 5 millimeters of viewing distance. For example, interference points are determined at each of several points at different distances from first optic fiber second end 66, within approximately 5 millimeters, thereby providing the data for approximately 5 millimeters in front of second end 66. The first and second fibers 42 and 44 may be stretched other amounts, to obtain the desired distance.

To obtain the interference data, detecting element 52 first detects the light interference patterns or interferences, between the reflected first light beam A and reflected second light beam B, and transmits interference data representative of such interferences to computer 54. Computer 54 utilizes the interference data to determine the safety of advancing guide wire 28.

In one alternative, if detecting element 52 generates interference data representative of a loss of signal through first optic fiber 42, the optical path lengths along first and second optic fibers 42 and 44 may be varied by expanding PZTs 48 and 50 to reestablish a signal at a new distance from first optic fiber second end 66.

In one embodiment, computer 54 generates data from such tissue and displays a representative pseudo image on screen 74. Particularly, computer 54 utilizes the interference data generated at various points in the tissue to generate image data representative of a substantially linear image profile of the examined tissue. Computer 54 also may utilize the interference data to generate and transmit control signals to a monitor while an operator guides guide wire 28 by hand. Alternatively, the control signals may be transmitted to a control device attached to guide wire 28.

Guide wire bore 34 may, for example, have a diameter of approximately 0.010 inches. First and second optic fibers 42 and 44 may, for example, have a respective diameter of approximately 0.007 inches.

The above described guide wire provides a guidance system to determine the safety of advancing the guide wire further into the vessel. The guide wire also provides information to help an operator distinguish among the types of obstructions which might be obstructing advancement of the guide wire. However, it is to be understood that the above described guide wire is exemplary and other embodiments are possible.

Many other variations are contemplated and possible. For example, in another embodiment, the guide wire may be made with a harder and less floppy end (for example, made of hardened steel) to make it more suitable to go through a partially occluded artery. The guide wire may also be coated with friction reducing material such as, for example, a polymer or a hydrophilic coating as known in the art. The coating reduces the surface friction to ease advancing the guide wire further into the vessel. The guide wire may also include a thin metal wire positioned next to the fiber optic which can be pulled back making the guide wire end very floppy. The metal wire, when extended, stiffens the more distal portion of the guide wire.

From the preceding description of the present invention, it is evident that the objects of the invention are attained. Although the invention has been described and illustrated in detail, it is to be clearly understood that the same is intended by way of illustration and example only and is not be taken by way of limitation. Accordingly, the spirit and scope of the invention are to be limited only by the terms of the claims.

What is claimed is:

1. A guide wire assembly comprising:

a guide wire having a first end, a second end, and a bore extending between said first end and said second end; and at least one guidance system coupled to said guide wire, said guidance system comprising a low coherence illumination source, a beam splitter, a first optic fiber having a length, a first end and a second end, a second optic fiber having a length, a first end and a second end, a fixed reflector on said second optic fiber second end, and a detecting element communicatively coupled to said first ends of said first and second optic fibers, said beam splitter configured to split a first light beam into a second light beam and a third light beam, said first optic fiber wrapped around a first piezo electric transducer, said second optic fiber wrapped around a second piezo electric transducer, wherein said first piezo electric transducer alters said first optic fiber length and said second piezo electric transducer alters said second optic fiber length to produce interferometric data, said first optic fiber coupled to said guide wire so that said second end of said first optic fiber is adjacent said second end of said guide wire, said detecting element configured to determine interference between the second light beam reflected through said first optic fiber and the third light beam reflected through said second optic fiber.

2. A guide wire assembly in accordance with claim 1 wherein said detecting element is a photodetector.

3. A guide wire assembly in accordance with claim 1 wherein said first optic fiber is wrapped around said first piezo electric transducer approximately 1000 times.

4. A guide wire assembly in accordance with claim 1 wherein said second optic fiber is wrapped around said second piezo electric transducer approximately 1000 times.

5. A guide wire assembly in accordance with claim 1 wherein said first optic fiber is wrapped around said first piezo electric transducer approximately 300 times.

6. A guide wire assembly in accordance with claim 1 wherein said second optic fiber is wrapped around said second piezo electric transducer approximately 300 times.

7. A guide wire assembly in accordance with claim 1 wherein said first optic fiber extends through said guide wire bore.

8. A guide wire assembly in accordance with claim 1 wherein said reflector comprises a noble metal surface on said second optic fiber second end.

9. A guide wire assembly in accordance with claim 1 wherein said reflector comprises a gold surface on said second optic fiber second end.

10. A guide wire assembly in accordance with claim 1 wherein said beam splitter comprises an illumination source input, a first beam output, a second beam output, and a combined beam output.

11. A guide wire assembly in accordance with claim 10 wherein said illumination source is coupled to said illumination source input, said first end of said first optic fiber is coupled to said first beam output, said first end of said second optic fiber is coupled to said second beam output, and said combined beam output is coupled to said photodetector.

12. A guide wire assembly in accordance with claim 1 wherein said first piezo electric transducer and said second piezo electric transducer are connected in said guidance system in reverse parallel configuration.

13. A guide wire assembly comprising:
a guide wire having a first end, a second end, and a bore extending between said first end and said second end; and
at least one guidance system coupled to said guide wire; said guidance system comprising an illumination source, a beam splitter, a first optic fiber, a second optic fiber, a fixed reflector on an end of said second optic fiber, a first lengthening means for altering the length of said first optic fiber, a second lengthening means for altering the length of said second optic fiber, and a detecting element configured to determine interference between a second light beam propagating through said first optic fiber and a third light beam propagating through said second optic fiber, said beam splitter configured to split a first light beam into said second light beam and said third light beam and then recombine said second light beam and said third light beam into a fourth light beam.

14. A guide wire assembly in accordance with claim 13 wherein said first lengthening means is a piezo electric transducer.

15. A guide wire assembly in accordance with claim 13 wherein said second lengthening means is a piezo electric transducer.

16. A guide wire assembly in accordance with claim 13 wherein said first lengthening means and said second lengthening means are connected in said guidance system in reverse parallel configuration.

17. A method for advancing a guide wire through a blood vessel utilizing at least one interferometric guidance system, the guide wire including a first end, a second end, and a bore extending therebetween, each interferometric system including a first optic fiber having a second end and a length, a first lengthening means for altering the length of a first optic fiber, a second optic fiber having a second end including a fixed reflector and a length, a second lengthening means for altering the length of the second optic fiber, and a photodetector communicatively coupled to both the first optic fiber and the second optic fiber, the first lengthening means and the second lengthening means being connected in the guidance system in reverse parallel configuration, said method comprising the steps of:
extending the first optic fiber of at least one of the interferometric guidance systems through the guide wire bore;
inserting the guide wire at least partially into the blood vessel; and
extending the length of the first optic fiber by expanding the second lengthening means and contracting the first lengthening means.

18. A method in accordance with claim 17 wherein the interferometric guidance system comprises an interferometric guide wire system.

19. A method in accordance with claim 17 wherein the first lengthening means is a first piezo electric transducer and the second lengthening means is a second piezo electric transducer, and wherein extending the length of the first optic fiber of at least one of the interferometric guidance systems comprises the step of enabling the first piezo electric transducer.

20. A method in accordance with claim 19 wherein extending the length of the first optic fiber comprises the step of alternately enabling the first piezo electric transducer and disabling the first piezo electric transducer.

21. A method in accordance with claim 20 further comprising the step of extending the length of the second optic fiber.

22. A method in accordance with claim 21 wherein extending the length of the second optic fiber comprises the step of alternately enabling the second piezo electric transducer and disabling the second piezo electric transducer.

23. A method in accordance with claim 17 wherein the interferometric system further comprises a beam splitter, the beam splitter configured to split a first light beam into a second light beam and a third light beam and then to recombine the second light beam and the third light beam into a fourth light beam.

* * * * *